United States Patent [19]

Lovaas

[11] Patent Number: 4,889,487
[45] Date of Patent: Dec. 26, 1989

[54] ENDODONTIC FILES

[76] Inventor: Leeland M. Lovaas, 40 Via Larga Vista, Bonsall, Calif. 92003

[21] Appl. No.: 275,213

[22] Filed: Nov. 23, 1988

[51] Int. Cl.$^4$ ............................................. A61C 5/02
[52] U.S. Cl. ......................................................... 433/102
[58] Field of Search ................................. 433/102, 4

[56] References Cited

U.S. PATENT DOCUMENTS

| | | | |
|---|---|---|---|
| 31,331 | 2/1861 | Sheehan | 433/144 |
| 273,821 | 3/1883 | Crosthwaite | 433/144 |
| 318,173 | 5/1885 | Donaldson | 433/102 |
| 322,265 | 7/1885 | Donaldson | 433/102 |
| 408,926 | 8/1889 | Palmer | 132/76.4 |
| 940,351 | 11/1909 | Neugebauer | 137/76.4 |
| 1,586,441 | 12/1923 | Blom | 132/73.2 |
| 1,771,182 | 2/1928 | Lentulo | 76/24 R |
| 2,214,954 | 5/1935 | Crater | 29/78 |
| 2,233,438 | 3/1941 | Troya | 132/76.4 |
| 2,490,647 | 5/1947 | Norman | 132/76.4 |
| 3,330,040 | 7/1967 | Kahn | 32/57 |
| 4,109,384 | 8/1978 | Dorian | 32/40 |
| 4,552,531 | 11/1985 | Martin | 433/147 |

*Primary Examiner*—Robert Peshock
*Attorney, Agent, or Firm*—Jerry R. Seiler

[57] ABSTRACT

An endodontic file comprises a flexible filing shaft having a filing portion extending along the length thereof from a first end, said filing portion having one or more elongated, bow-shaped bends therealong for being urged against a root canal for enlarging or shaping said canal.

18 Claims, 2 Drawing Sheets

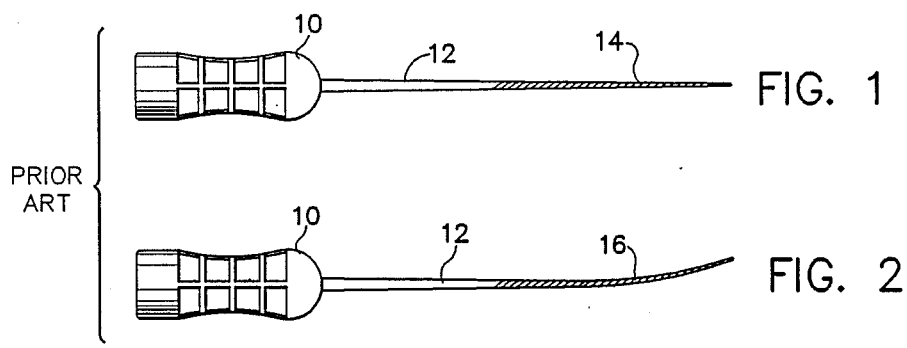
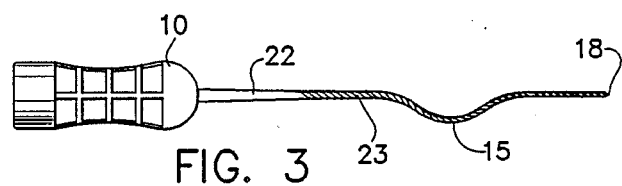
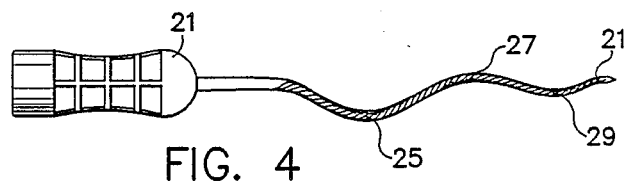
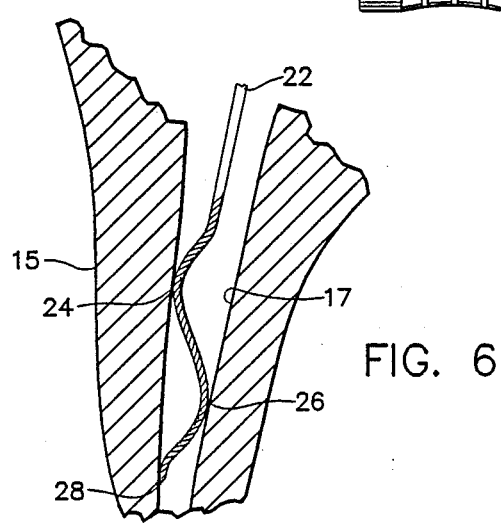
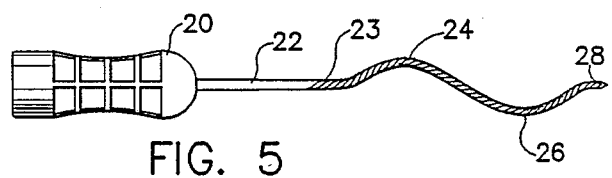

ENDODONTIC FILES

BACKGROUND OF THE INVENTION

Endodontic files having a tapered flexible shaft with cutting edges thereon have been used for many years for enlarging a root canal. Heretofore, these instruments have generally been of the type illustrated in FIGS. 1 and 2 incorporating a handle 10 secured at one end of the shaft 12 opposite a somewhat pointed tip. Along a portion of the length of the shaft are the cutting edges or surfaces, normally spiral, serrated, or impregnated with sharp cutting material, used for enlarging and cleaning out the canal in the root of the tooth prior to filling it with inert material. The cutting or working portions of the prior art shafts have comprised a straight portion 14 illustrated in FIG. 1 or curved portion 16 shown in FIG. 2. An example of such an instrument is illustrated in U.S. Pat. No. 4,536,159. Although these prior art devices are suitable for their intended purpose, because of the relatively straight shaft, it is difficult to work on and enlarge specific areas along the root canal. It is to the improvement of such an endodontic root canal enlarging device that the present invention is directed.

SUMMARY OF THE INVENTION

The present invention is directed to an improved endodontic file in which the elongated filing shaft has one or more elongated bow-shaped bends along its length. A preferred file embodiment has two or more adjacent, elongated and opposite bow-shaped bends therelong. The invention also includes the method of enlarging a root canal using such a file. In addition, a tool for crimping a filing shaft to produce a file of the invention is also included. More specific features and the advantages of such devices will be disclosed in the following detailed description.

BRIEF DESCRIPTION OF THE DRAWINGS

FIGS. 1 and 2 show endodontic file devices of the prior art;

FIG. 3 shows a file of the invention having a single bow-shaped bend;

FIG. 4 illustrates a file of the invention having three contiguous bends along the filing shaft;

FIG. 5 illustrates a file of the invention having two bends;

FIG. 6 shows a portion of the filing shaft of a file of the invention in a root canal illustrating the use thereof for enlargement;

DETAILED DESCRIPTION OF THE INVENTION

Figure 7:
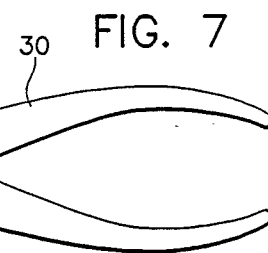
FIG. 7 shows a crimping tool of the invention.

FIG. 3 illustrates a first embodiment of the invention comprising a file having a handle 10, a shaft 22 with a filing portion 23, and a single bow-shaped bend 15 located along the filing portion length. The radius (depth) of the bend as well as its length and its position along the filing shaft relative to tip 18 may be varied depending on the depth and shape of the tooth root canal to be worked on. For example, where the canal is relatively shallow, the bend may desirably be located closer to the tip as compared to a deeper canal. Similarly a greater bend radius may be preferred for enlarging a wider canal. Although each of the devices shown in FIGS. 3-5 have a handle, the invention is not so limited and includes files having no handle in which the shaft is designed to be used with the dental drill apparatus or an ultrasonic drill in which the shaft is secured in the handpiece.

A second endodontic file embodiment is illustrated in FIG. 5 comprising a handle 20 and a flexible filing shaft 22 having a serrated filing portion 23. In this embodiment, the filing portion incorporates two adjacent, elongated and opposite bow-shaped bends 24 and 26 and terminates at tip 28. Bow-shaped bends 24 and 26 are opposite, that is, they lie or extend along the same plane, but are bent or bowed outwardly in opposite directions from the axis extending along the upper portion of the filing shaft 22 and tip 28. In this device, the bends may be substantially equal in their radius or maximum distance from the elongated axis and also of substantially equal length of their arc. However, it may be preferred to have different arc lengths and/or radii of each of the respective bends for specific requirements for enlarging a root canal. For example, for many applications, it is desirable to have a smaller radius or tighter bend near the tip for working the smaller, deeper portion of a root canal and a larger radius second bend further along the shaft length from the tip. The use of such a file is shown in FIG. 6. The bends may be individually shaped as desired to meet a particular type of root canal enlargement as will be understood by those skilled in the art. Such a method and means for producing an endodontic file in which the size, shape, and number of bends may be selected by the user is a significant improvement and advantage of the present invention.

Another embodiment of the invention is illustrated in FIG. 4, this instrument having three adjacent elongated bow-shaped bends 25, 27 and 29. Again, preferably, the bends lie in a single plane so that bends 25 and 29 are bow-shaped in the same direction along the same plane while bend 27 is opposite and also co-planar. Where the bends lie along the same plane, by rotating the files shown in FIGS. 3-5 about 90° along the upper shaft axis, the bends would disappear to a viewer observing to the same angle. Alternatively, these bends may extend in different planes. The embodiment of FIG. 4 may also be described by bends 25 and 29 being recurves contiguous with and extending from central bow-shaped bend 27. Again, it is usually advantageous to use a smaller bend nearer tip 21 for preparing tapered root canals. In the embodiment, bend 29 is smaller than either bend 27 or 25, and bend 25 is larger than bend 27. Thus, the bends increase in size between tip 21 and handle 31. Other devices may include additional curves or bends of the same or different sizes, which may be selectively formed to meet specific endodontic root canal enlarging needs.

In FIG. 6, a cross-section of a portion of a tooth root 15 having a canal 17 is shown with an instrument of FIG. 5 used for enlarging the canal. Shaft 22 is shown extending into the canal with first bend 24 being urged against one side of the canal and opposite bend 26 urged against the other side of the canal. The filing surface along the straight portion of the shaft adjacent tip 21 is also urged along the canal side. Thus, the endodontist may exert filing pressure at three different positions simultaneously when using such an instrument. With the filing shaft being somewhat flexible axially it will be evident that a user can move the file upwardly and downwardly reciprocally in the canal and with the bends forced against the length of the interior wall, a much greater control for enlarging the canal may be achieved. The file may also be rotated so that the user is able to be selective in filing and enlarging different portions or areas of the canal wall.

Figure 8:
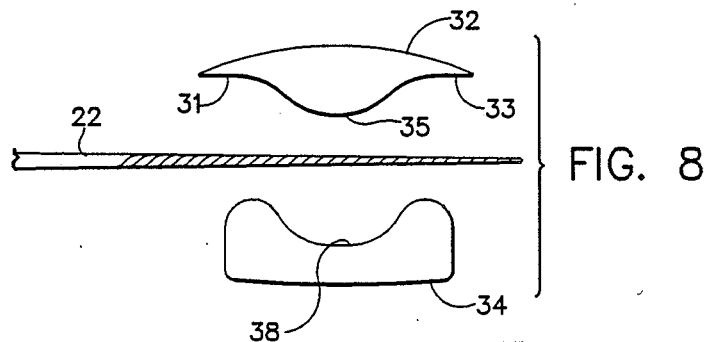
FIG. 8 is a top view of the crimping jaws of the crimping tool of FIG. 7 with a straight file portion therebetween prior to being crimped.
Figure 9:
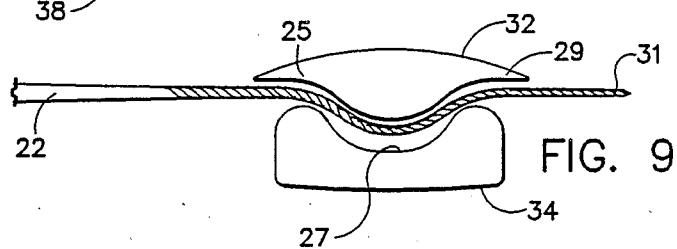
FIG. 9 shows the crimping tool jaws forced together for crimping the filing shaft.

FIG. 7 illustrates a device for crimping a filing shaft to form a file as previously described comprising a crimping tool 30 having first and second jaws 32 and 34. The crimping tool is similar to pliers with the opposing jaws being shaped to achieve the bow-shaped bends as previously described along the file length. In FIG. 8, first jaw 32 having a bow-shaped crimp forming surface comprises a convex arched-shaped ridge 35 with recurve surfaces 31 and 33 extending along opposite sides of the ridge. The opposite crimping surface of second jaw 34 has a concave arched-shaped cavity 38 which receives the convex ridge 35 when the jaws are urged together in the crimping operation as illustrated in FIG. 9. The file shaft is placed between the jaws so that the elongated shaft axis is substantially or generally normal to the axis of the elongated convex ridge. To form a device of the invention as shown in FIG. 3, the user simply inserts the serrated portion of an endodontic filing shaft 22 between the open jaws as illustrated in FIG. 8, holding the file with one hand, and with the other hand, holding and squeezing the crimping tool handles so that the opposite jaws are urged together.

Figure 10:
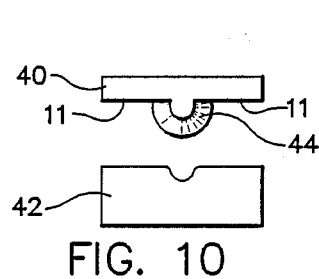
FIGS. 10-12 show another crimping tool embodiment.
Figures 11, 12:
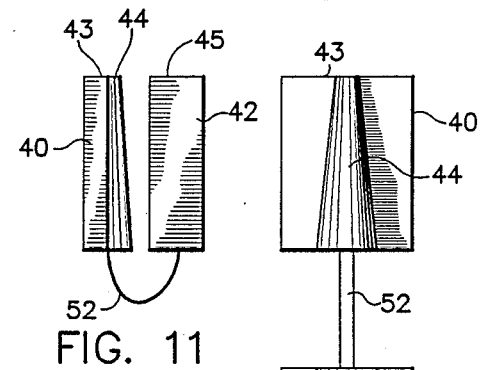

In FIGS. 10–12 there is shown another embodiment of a crimping tool incorporating a pair of opposite crimp jaws 40 and 42. In FIG. 10, the device is viewed from the top end of the crimping jaws, FIG. 11 shows the side view thereof, and FIG. 12 is a plan view of the open jaw surfaces. A spring connector 52 is biased to keep the jaws slightly spread when not in use as shown in FIG. 11. The connector may be made of a spring metal or even a plastic unitary with the jaw components, such that the entire tool could be relatively inexpensive to mold from plastic stock. In this embodiment, the convex crimping ridge 44 has a narrowed radius at the top and is tapered along its length to a wider bottom in the shape of a segment or section of a frustum. The opposite jaw 42 has a convex cavity 46, also gradually tapered, so that ridge 44 will be received and nest therein when the jaws are closed. Using such a device having a tapered ridge and cavity the user can select the radius and length of the bow-shaped bends by placing the shaft higher or lower in the crimping tool to achieve the desired bend radius and length. Thus, if the file shaft is placed closer to the upper end of top jaw surfaces 43 and 45 the radius and length of the bow-shaped bend will be smaller as compared to placing the file and crimping it near the bottom of the jaws. Accordingly, such a tool may be shaped so that the user may be selective in performing the desired shapes and sizes of the bends along the file length. Moreover, using such crimping tools as illustrated also allows the user to select the location of the bends along the file length as desired. Although the radius of the ridge and cavity are shown as being gradually tapered, the taper may be stepped or segmented. In such a device, a plurality of different ridge segments, each having a different radius, may be present on one jaw, preferably stepped from narrow to larger radius, with a concave cavity similarly located on the opposite jaw. Such a device is equivalent to that shown and may allow the user to more easily select specific radius bends.

Figure 13:
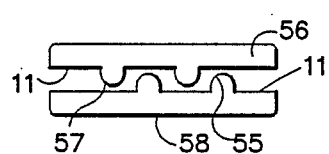
FIG. 13 illustrates yet another crimping tool design.

In FIG. 13 yet another crimping tool embodiment is illustrated in which multiple bends may be achieved in a single crimping action. Using the device shown, crimping a shaft between jaws 56 and 58 will result in four bends being formed simultaneously. Such a multiple crimping tool may incorporate features of the previously described tools. These as well as other embodiments and advantages within the purview of the invention will be evident to those skilled in the art.

I claim:

1. An endodontic file comprising a flexible filing shaft having a filing portion extending along the length thereof from a first end, said filing portion having one or more bow-shaped bends therealong for being urged against a root canal for enlarging or shaping said canal.

2. The file of claim 1 having two or more of said bends.

3. The file of claim 2 wherein said bends have substantially equal radius.

4. The file of claim 2 wherein said bends are of substantially equal length.

5. The file of claim 3 wherein said bends are of substantially equal length.

6. The file of claim 1 comprising two of said bends said bends being contiguous.

7. The file of claim 1 comprising three contiguous bends, wherein the adjacent bends are bowed in opposite directions.

8. The file of claim 1 including a handle attached to a second end of said shaft.

9. The file of claim 5 wherein said bends are bowed in opposite directions along the same plane.

10. The file of claim 7 wherein each of said bends is bowed in a different plane, said planes intersecting the elongated axis of said shaft.

11. An endodontic file comprising a flexible filing shaft having a filing portion extending therealong from a first end, said filing portion having a bow-shaped bend therealong, and a first and a second recurve contiguous with and extending from opposite ends of said bend along said shaft.

12. The file of claim 11 wherein said recurves are of substantially equal radius.

13. The file of claim 12 wherein said recurves are of substantially equal length.

14. The file of claim 11 including a handle secured to a second end of said shaft.

15. An endodontic file comprising a flexible filing shaft having a filing portion extending therealong from a first, generally pointed end, said filing portion having a plurality of bow-shaped bends therealong, each of said bends having a different radius.

16. The file of claim 15 wherein said bow-shaped bends comprise a first bend having a first radius and a second bend having a second radius, said first radius being smaller than said second radius and wherein said first bend is closer to said pointed end than said second bend.

17. The method of filing a root canal in a tooth comprising introducing the filing shaft of the file of claim 2 into the interior of the route canal until both of said bends are located in and urged against the interior wall of said canal, and reciprocally moving the file along said root canal to enlarge said canal.

18. The method of claim 17 including rotating said file axially during said reciprocal movement.

* * * * *